(12) United States Patent
Specht et al.

(10) Patent No.: US 7,653,439 B2
(45) Date of Patent: Jan. 26, 2010

(54) ELECTRODE STRUCTURE AND METHODS FOR MAKING AND USING SAME

(75) Inventors: Heiko Specht, Hanau (DE); Frank Krüger, Nidderau (DE)

(73) Assignee: W.C. Heraeus GmbH, Hanau (DE)

( * ) Notice: Subject to any disclaimer, the term of this patent is extended or adjusted under 35 U.S.C. 154(b) by 598 days.

(21) Appl. No.: 11/015,629

(22) Filed: Dec. 17, 2004

(65) Prior Publication Data

US 2005/0154436 A1  Jul. 14, 2005

(30) Foreign Application Priority Data

Dec. 19, 2003  (DE)  ................. 103 60 624

(51) Int. Cl.
*A61N 1/05* (2006.01)
(52) U.S. Cl. ............... 607/116; 607/118; 600/373; 600/377; 600/386; 427/2.1; 427/2.24; 428/35.7; 428/35.8
(58) Field of Classification Search ......... 607/116–138; 600/373–391; 427/2.1, 2.24; 428/35.7, 35.8
See application file for complete search history.

(56) References Cited

U.S. PATENT DOCUMENTS

| | | | |
|---|---|---|---|
| 5,178,957 A | 1/1993 | Kolpe et al. | |
| 5,324,322 A | 6/1994 | Grill, Jr. et al. | |
| 5,683,443 A | 11/1997 | Munshi et al. | |
| 5,720,099 A | 2/1998 | Parker et al. | |
| 6,266,568 B1 | 7/2001 | Mann et al. | |
| 6,374,143 B1 | 4/2002 | Berrang et al. | |
| 7,051,419 B2 * | 5/2006 | Schrom et al. | ........... 29/594 |
| 2001/0029366 A1 * | 10/2001 | Swanson et al. | ........... 606/29 |
| 2003/0036790 A1 | 2/2003 | Corbett et al. | |
| 2003/0195601 A1 | 10/2003 | Hung et al. | |
| 2004/0127966 A1 * | 7/2004 | Frericks et al. | ........... 607/116 |

FOREIGN PATENT DOCUMENTS

| | | |
|---|---|---|
| DE | 35 07 623 A1 | 9/1986 |
| WO | WO 02/087685 A2 | 11/2002 |
| WO | WO 02/089907 A1 | 11/2002 |

\* cited by examiner

*Primary Examiner*—Carl H Layno
*Assistant Examiner*—Deborah Malamud
(74) *Attorney, Agent, or Firm*—Panitch Schwarze Belisario & Nadel LLP

(57) ABSTRACT

An electrode structure made of noble metal or a noble metal alloy having a thickness of ≦100 μm is provided for implants. The electrode structure has an electrode core made of gold, silver, copper, or an alloy of at least two of these elements, and the electrode core is completely encased by a first coating, which is formed from platinum, iridium, or ruthenium.

9 Claims, 4 Drawing Sheets

ELECTRODE STRUCTURE AND METHODS FOR MAKING AND USING SAME

BACKGROUND OF THE INVENTION

The invention relates to an electrode structure made of a noble metal or a noble metal alloy having a thickness of ≦100 μm for implants, as well as to three methods for its production. The invention further relates to the use of such an electrode structure.

Electrode arrangements made of noble metal are known, for example, from International patent application publication WO 02/089907 A1. There, electrode structures are formed from platinum film and are fixed on a carrier made of plastic material. Such electrode arrangements are used, for example, for cochlear implants.

U.S. Pat. No. 6,266,568 B1 discloses an expandable cochlear electrode arrangement and a method for its production. There, a plurality of electrode contacts spaced from each other are arranged on a flexible carrier.

German published patent application DE-OS 35 07 623 A1 discloses a long-term implantable sheet electrode having a physiologically inert matrix made of flexible plastic, which is coated with an electrical conductor, for example made of platinum. The coating is there formed galvanically or by vapor deposition.

It is now an object of the invention to make available another electrode structure for implants, which can be produced simply and economically. Furthermore, suitable methods for its production, as well as its use, should be provided.

BRIEF SUMMARY OF THE INVENTION

The object is achieved for the electrode structure in that this structure has an electrode core made of gold, silver, copper, or an alloy of at least two of these elements, and that the electrode core is completely encased by a first coating, which is formed from platinum, iridium, or ruthenium.

Such an electrode structure is economical, because it has a ductile electrode core with good conductivity made of a more economical material, which is merely encased by a thin, more expensive coating, which is corrosion-resistant and biocompatible. Optionally, an alloy formation can be carried out between the electrode core and the first coating by a heating process.

It has proven effective if the electrode core has a thickness in a range of about 5 μm to 99.8 μm. For the first coating, a thickness in a range of about 100 nm to about 5 μm has proven effective. Forming the electrode structure with a thickness in a range of about 7 μm to about 30 μm is particularly preferred.

Preferably, a second coating, which is different from the first coating and which is made of ruthenium, ruthenium oxide, iridium, iridium oxide, platinum, or titanium nitride, is formed on the side of the first coating facing away from the electrode core. Here, it has proven effective if the second coating only covers parts of the first coating.

The object is further realized in a first method, wherein:
a) an electrically insulating surface of a substrate is coated with a metal layer, the metal layer is then coated with photoresist, and the photoresist is structured,
b) a first part of the first coating is electroplated on the now exposed regions of the metal layer,
c) the electrode core is electroplated on the first part of the first coating,
d) the structured photoresist is then removed from the metal layer,
e) the metal layer is removed from the electrically insulating surface of the substrate in the regions which are not covered by the first part of the first coating,
f) the part of the electrode core still free up to now from the first coating is electroplated with a second part of the first coating,
g) the electrode structure including the metal layer is detached from the electrically insulating surface of the substrate, and
h) the metal layer is then removed from the electrode structure.

The object is further realized in a second method, wherein:
a) an electrically insulating surface of a substrate is provided with a mask and a metal layer is formed by cathode sputtering or vapor deposition on the regions of the electrically insulating surface not covered with the mask,
b) a first part of the first coating is generated on the metal layer by cathode sputtering or vapor deposition,
c) the electrode core is then formed by cathode sputtering or vapor deposition on the first part of the first coating,
d) the mask is then removed,
e) at least the part of the electrode core still free up to now from the first coating is electroplated with a second part of the first coating and,
f) the electrode structure is then detached from the electrically insulating surface of the substrate, in which the metal layer is removed.

The object is further realized in a third method, wherein:
a) an electrically insulating surface of a substrate is coated with a structured metal layer, which forms a first part of the first coating,
b) the first part of the first coating is provided with a mask, and the electrode core is formed only on the first part of the first coating by cathode sputtering or vapor deposition,
c) the part of the electrode core still free up to now from the first coating is then electroplated with a second part of the first coating, and
d) the electrode structure is then detached from the electrically insulating surface of the substrate.

Such methods are excellently suited to economical and fast production of the electrode structure according to the invention.

In this way, the electrode core can be encased with several different coatings. To form a second coating on the first coating, for example with the third method, the electrically insulating surface of a substrate must then be coated with a structured metal layer, which forms a first part of the second coating, and then the first part of the first coating is formed thereon. After forming the electrode core and the second part of the first coating, a second part of the second coating is finally formed. Corresponding masks are used accordingly.

Here, it has proven effective, for the three methods according to the invention, to form the electrically insulating surface of the substrate from glass or plastic. A suitable metal layer can be formed preferably from copper or gold.

Use of the electrode structure according to the invention for a stimulation electrode, cochlear electrode, or retinal electrode is ideal.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
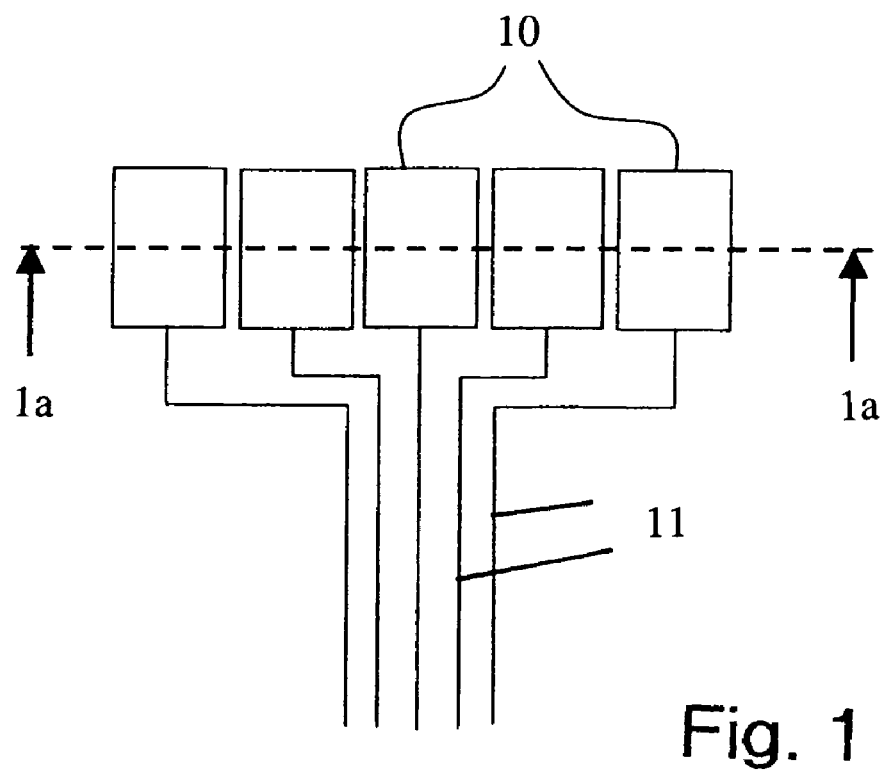
FIG. 1 is a schematic diagram in plan view of several electrode structures with electrical supply lines.

FIG. 1 shows several electrode structures 10, here in an arbitrarily selected arrangement relative to each other. Each electrode structure 10 is connected to an electrical line 11. However, obviously any other arrangement can also be selected.

Figure 1A:
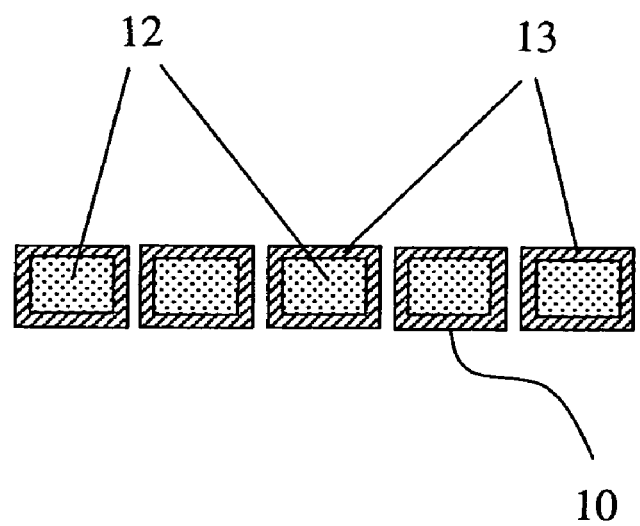
FIG. 1a is a schematic diagram in sectional view 1a-1a of the electrode structures from FIG. 1, FIGS. 2a to 2d illustrate schematically steps of the third method for producing an electrode structure according to the invention.

FIG. 1a shows the section 1a-1a from FIG. 1. Here, it can be seen that an electrode structure 10 is constructed of an electrode core 12 and a first coating 13, which completely surrounds the electrode core 12.

Figure 2A:
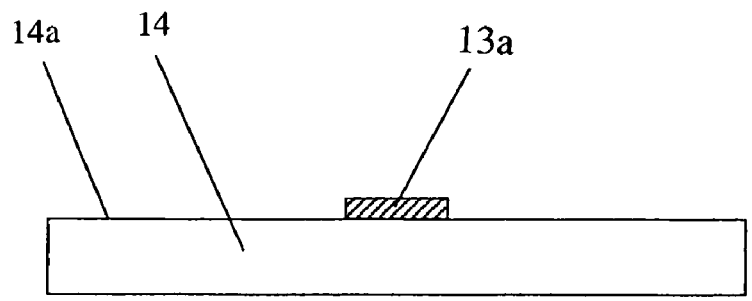
Figure 2B:
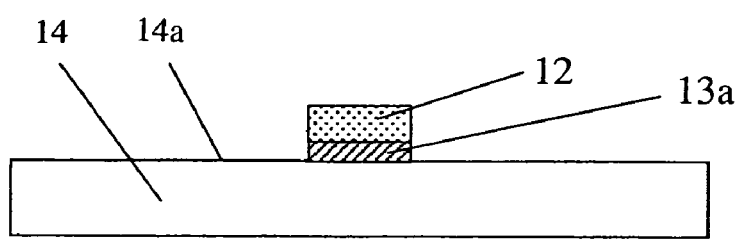
Figure 2C:
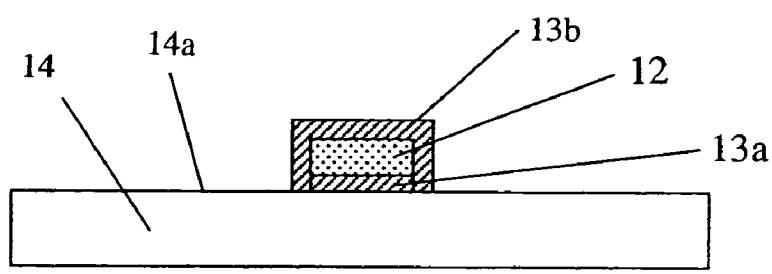
Figure 2D:
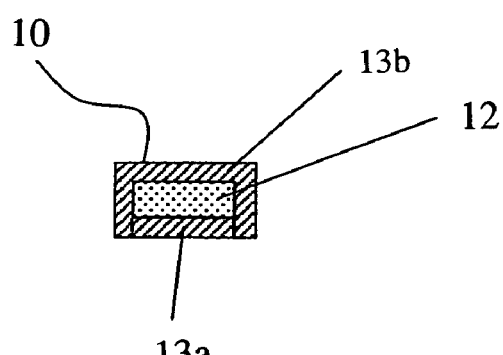

FIGS. 2a-2d show the sequence of a third method according to the invention for producing an electrode structure 10 according to the invention. In FIG. 2a, a first part 13a of a first coating made of iridium is vapor deposited on an electrically insulating surface 14a of a substrate 14. FIG. 2b illustrates that an electrode core 12 made of gold is vapor deposited on the first part 13a of the first coating. FIG. 2c shows that a second part 13b of the first coating made of iridium is galvanically deposited onto the electrode core 12. FIG. 2d shows finally the completed electrode structure 10 detached from the substrate 14. The masks necessary for vapor deposition of the first part 13a of the first coating and the electrode core 12, which cover the regions of the substrate 14 lying next to these parts, are not shown.

Figure 3A:
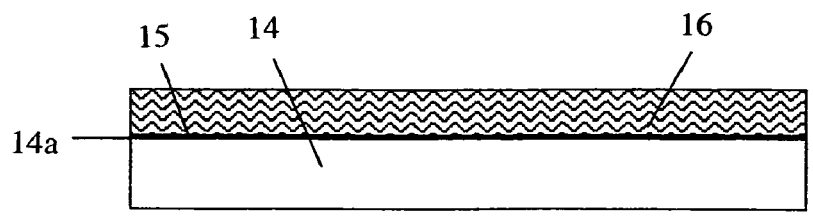
FIGS. 3a to 3h illustrate schematically steps of the first method for producing an electrode structure according to the invention.
Figure 3B:
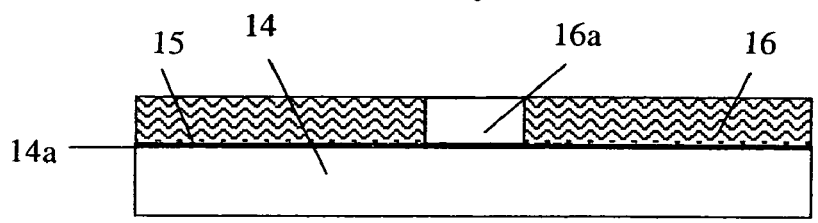
Figure 3C:
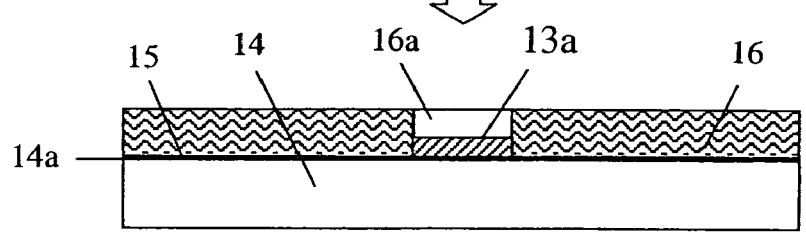
Figure 3D:
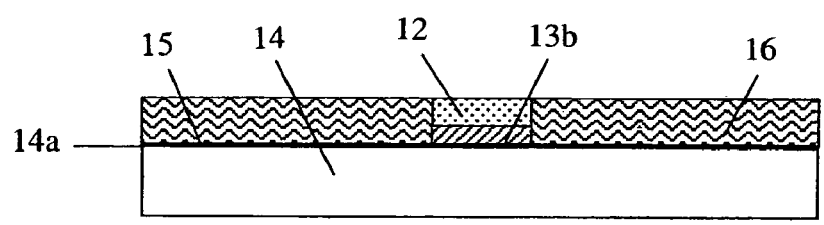
Figure 3E:
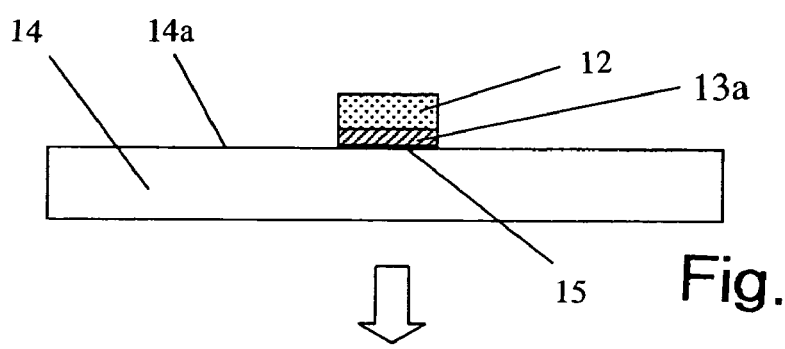
Figure 3F:
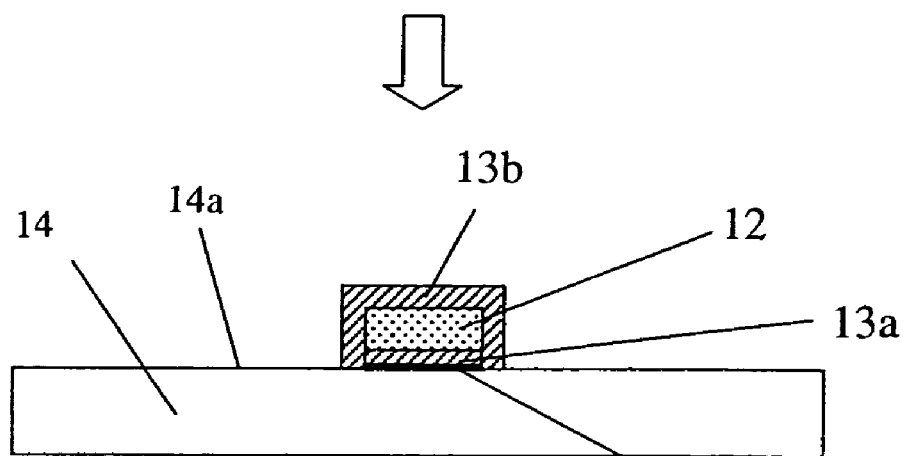
Figure 3G:
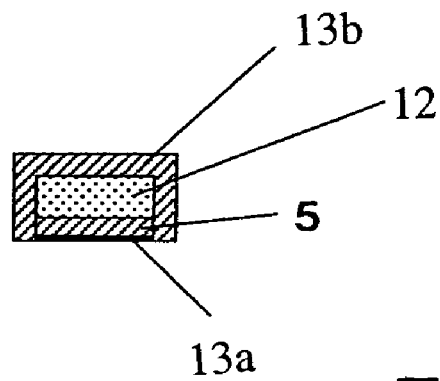
Figure 3H:
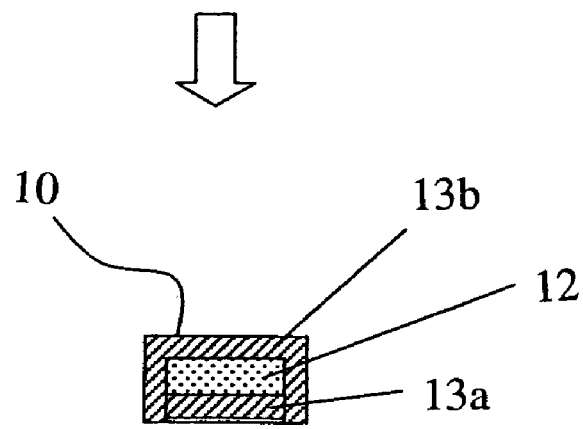

FIGS. 3a-3h show the sequence of a first method according to the invention for producing an electrode structure 10 according to the invention. In FIG. 3a, an electrically insulating surface 14a made of glass for a substrate 14 is coated with a metal layer 15 made of copper and a photoresist 16. The photoresist 16 is structured such that the metal layer 15 is partially exposed via openings 16a in the photoresist 16 (see FIG. 3b). In the opening 16a, a first part 13a of a first coating made of platinum is then galvanically deposited (see FIG. 3c). FIG. 3d illustrates that an electrode core 12 made of copper is then galvanically deposited on the first part 13a of the first coating. FIG. 3e shows that the photoresist 16 and also the resulting exposed parts of the metal layer 15 are now removed. Then, a second part 13b of the first coating made of platinum is galvanically generated (see FIG. 3f). After removing the substrate 14, a part of the metal layer 15 (see FIG. 3g), which is yet to be removed, still remains on the electrode structure. FIG. 3h shows finally the completed electrode structure 10 having the electrode core 12 and a first coating 13a, 13b.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for producing an electrode structure (10) for implants, comprising a noble metal or a noble metal alloy having a thickness of $\leq 100$ µm, wherein the electrode structure (10) has an electrode core (12) comprising an element selected from the group consisting of gold, silver, copper, and alloys of at least two of these elements, and wherein the electrode core (12) has a thickness in a range of about 5 µm to 99.8 µm and is encased completely by a first coating (13; 13a, 13b) comprising at least one element selected from the group consisting of platinum, iridium, and ruthenium, the method comprising:
    a) coating an electrically insulating surface (14a) of a substrate (14) with a metal layer (15), then coating the metal layer (15) with a photoresist (16), and structuring the photoresist (16),
    b) galvanically generating a first part (13a) of the first coating on regions of the metal layer (15) exposed by the structured photoresist,
    c) galvanically forming the electrode core (12) on the first part (13a) of the first coating,
    d) then removing the structured photoresist (16) from the metal layer (15),
    e) removing the metal layer (15) from the electrically insulating surface (14a) of the substrate (14) in regions not covered by the first part (13a) of the first coating,
    f) galvanically coating part of the electrode core (12) still free up to now from the first coating with a second part (13b) of the first coating,
    g) detaching the electrode structure (10) including the metal layer (15) from the electrically insulating surface (14a) of the substrate (14), and
    h) then removing the metal layer (15) from the electrode structure (10).

2. The method according to claim 1, wherein the electrically insulating surface (14a) of the substrate (14) comprises glass or plastic.

3. The method according to claim 1, wherein the metal layer (15) comprises copper or gold.

4. A method for producing an electrode structure (10) for implants, comprising a noble metal or a noble metal alloy having a thickness of $\leq 100$ µm, wherein the electrode structure (10) has an electrode core (12) comprising an element selected from the group consisting of gold, silver, copper, and alloys of at least two of these elements, and wherein the electrode core (12) has a thickness in a range of about 5 µm to 99.8 µm and is encased completely by a first coating (13; 13a, 13b) comprising at least one element selected from the group consisting of platinum, iridium, and ruthenium, the method comprising:
    a) providing an electrically insulating surface (14a) of a substrate (14) with a mask, and forming a metal layer (15) by cathode sputtering or vapor deposition on regions of the electrically insulating surface (14a) not covered with the mask,
    b) generating a first part (13a) of the first coating by cathode sputtering or vapor deposition on the metal layer (15),
    c) then forming the electrode core (12) by cathode sputtering or vapor deposition on the first part (13a) of the first coating,
    d) then removing the mask,
    e) galvanically coating at least part of the electrode core (12) still free up to now from the first coating (3a, 3b) with a second part (13b) of the first coating, and
    f) then detaching the electrode structure (10) from the electrically insulating surface (14a) of the substrate (14) such that the metal layer (15) is removed.

5. The method according to claim 4, wherein the electrically insulating surface (14a) of the substrate (14) comprises glass or plastic.

6. The method according to claim 4, wherein the metal layer (15) comprises copper or gold.

7. A method for producing an electrode structure (10) for implants, comprising a noble metal or a noble metal alloy having a thickness of $\leq 100$ µm, wherein the electrode structure (10) has an electrode core (12) comprising an element selected from the group consisting of gold, silver, copper, and alloys of at least two of these elements, and wherein the electrode core (12) has a thickness in a range of about 5 μm to 99.8 μm and is encased completely by a first coating (13; 13*a*, 13*b*) comprising at least one element selected from the group consisting of platinum, iridium, and ruthenium, the method comprising:

a) coating an electrically insulating surface (14*a*) of a substrate (14) with a structured metal layer, which forms a first part (13*a*) of the first coating, b) providing the first part (13*a*) of the first coating with a mask, and forming the electrode core (12) by cathode sputtering or vapor deposition only on the first part (13*a*) of the first coating, c) then galvanically coating part of the electrode core (12) still free up to now from the first coating (3*a*) with a second part (13*b*) of the first coating, and d) then detaching the electrode structure (10) from the electrically insulating surface (14*a*) of the substrate (14).

8. The method according to claim 7, wherein the electrically insulating surface (14*a*) of the substrate (14) comprises glass or plastic.

9. An electrode structure (10) for implants, comprising a noble metal or a noble metal alloy having a thickness of $\leq 100$ μm, wherein the electrode structure (10) has an electrode core (12) comprising an element selected from the group consisting of gold, silver, copper, and alloys of at least two of these elements, wherein the electrode core (12) has a thickness in a range of about 5 μm to 99.8 μm and is encased completely by a first coating (13; 13*a*, 13*b*) comprising at least one element selected from the group consisting of platinum, iridium, and ruthenium, and wherein the electrode structure is in a form selected from the group consisting of stimulation electrodes, cochlear electrodes, and retinal electrodes.

* * * * *

UNITED STATES PATENT AND TRADEMARK OFFICE
CERTIFICATE OF CORRECTION

PATENT NO.       : 7,653,439 B2
APPLICATION NO.  : 11/015629
DATED            : January 26, 2010
INVENTOR(S)      : Specht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1197 days.

Signed and Sealed this

Twenty-third Day of November, 2010

David J. Kappos
*Director of the United States Patent and Trademark Office*